(12) United States Patent
Zimmermann et al.

(10) Patent No.: US 9,005,956 B2
(45) Date of Patent: Apr. 14, 2015

(54) METHOD FOR EXTRACTING PHOSPHOROUS FROM SOLIDS USING ACTIVE LEACHING AND PHOSPHATE-ACCUMULATING MICROORGANISMS

(75) Inventors: Jennifer Zimmermann, Aachen (DE); Wolfgang Dott, Aachen (DE)

(73) Assignee: Georg Fritzmeier GmbH & Co. KG, Großhelfendorf (DE)

( * ) Notice: Subject to any disclaimer, the term of this patent is extended or adjusted under 35 U.S.C. 154(b) by 936 days.

(21) Appl. No.: 13/057,455

(22) PCT Filed: Aug. 14, 2009

(86) PCT No.: PCT/EP2009/060562
§ 371 (c)(1),
(2), (4) Date: Apr. 6, 2011

(87) PCT Pub. No.: WO2010/018228
PCT Pub. Date: Feb. 18, 2010

(65) Prior Publication Data
US 2012/0103037 A1    May 3, 2012

(30) Foreign Application Priority Data

Aug. 15, 2008 (DE) .......................... 10 2008 038 886

(51) Int. Cl.
*B09B 3/00* (2006.01)
*B09C 1/10* (2006.01)
*C02F 3/00* (2006.01)
*C02F 3/02* (2006.01)
*C02F 3/34* (2006.01)
*D06M 16/00* (2006.01)
*C12P 39/00* (2006.01)
*C05B 13/06* (2006.01)
*C05B 15/00* (2006.01)
*C05D 9/02* (2006.01)
*C12P 3/00* (2006.01)
*C12P 9/00* (2006.01)

(52) U.S. Cl.
CPC ................ *C12P 39/00* (2013.01); *C05B 13/06* (2013.01); *C05B 15/00* (2013.01); *C05D 9/02* (2013.01); *C12P 3/00* (2013.01); *C12P 9/00* (2013.01); *Y10S 210/906* (2013.01)

(58) Field of Classification Search
CPC ... A01N 25/10; A01N 65/00; A01N 2300/00; A01N 25/24; A01N 37/46; A01N 63/02; A01N 59/00; A01N 59/26; C05B 15/00; C05B 13/06; B09B 3/00; B09C 1/10; C02F 3/00; C02F 3/02; C02F 3/34; D06M 16/00
USPC .......... 106/124.1; 134/26; 210/681, 620, 906; 424/405; 435/192, 262, 262.5, 264
See application file for complete search history.

(56) References Cited

U.S. PATENT DOCUMENTS

2003/0170654 A1 * 9/2003 Crocetti et al. ................... 435/6

FOREIGN PATENT DOCUMENTS

FR   2595687    9/1987
JP   2006-34141   2/2006

OTHER PUBLICATIONS

Recent advances in removing phosphorus from wastewater and its future use as fertilizer (1997-2003), Luz E. de-Bashan, Yoav Bashan, Water Research 38 (2004) 4222-4246.
"Selective enrichment and characterization of a phosphorous-removing bacterial consortium from activated sludge", J. Hollender, et al., Applied Microbiology and Biotechnology, vol. 58, Nr. 1, pp. 106-111 (Jan. 2002).
"Sequenced bioleaching and bioaccumulation of phosphorous from sludge combustion—A new way of resource reclaiming", J. Zimmermann and W. Dott, Advanced Materials Research, vols. 71-73, pp. 625-628, (2009).
"Growth stimulation of sulfur oxidizing bacteria for optimization of metal leaching efficiency of fly ash from municipal solid waste incineration", W. Krebs, et al., Hydrometallurgy, vol. 59, Nr. 2-3, pp. 283-290 (Feb. 2001).
"Bacterial leaching of metals from sewage sludge by indigenous iron-oxidizing bacteria", R. D. Tyagi, et al., Environmental Pollution, vol. 82, Nr. 1, pp. 9-12 (1993).
Database WPI Week 200616, Thomson Scientific, London, GB, AN 2006-149331.

* cited by examiner

*Primary Examiner* — Debbie K Ware
(74) *Attorney, Agent, or Firm* — O'Melveny & Myers LLP

(57) ABSTRACT

The present invention relates to a method of selectively obtaining phosphorus from solids containing heavy metals and phosphate. In this method, the solid is treated under acidic aerobic conditions using microorganisms comprising leaching microorganisms and polyphosphate-accumulating microorganisms, so that the heavy metals and the phosphates are released from the solid and the released phosphates may be taken up by the polyphosphate-accumulating microorganisms. The phosphorus-enriched biomass that is obtained in this manner is separated and may be utilized, e.g., as organic fertilizer.

15 Claims, 3 Drawing Sheets

METHOD FOR EXTRACTING PHOSPHOROUS FROM SOLIDS USING ACTIVE LEACHING AND PHOSPHATE-ACCUMULATING MICROORGANISMS

This Application is a 371 of PCT/EP2009/060562, filed Aug. 14, 2009.

BACKGROUND OF THE INVENTION

1. Field of the Invention

The invention relates to a method of selectively obtaining phosphorus from heavy metal- and phosphate-containing solid material.

2. Description of Related Art

Phosphorus is a limiting nutrient to the growth of plants, and as it exclusively occurs in bound form, it is mined in the form of phosphate ore from deposits which are exhaustable in the form presently known. Mined phosphates are mainly processed to form plant available mineral fertilizer.

The treatment of waste water from household or industry results in the generation of sewage sludge which may be utilized in agriculture because of the nutrients nitrogen and phosphorus contained therein. As the sewage sludge does, however, also contain pollutants such as heavy metals, e.g. lead and cadmium, agricultural utilization of sewage sludge is increasingly challenged. Attempts are accordingly undertaken to largely clean phosphates contained in the sewage sludge from heavy metals by selective recovery.

Phosphorus is removed or eliminated from waste water in undissolved form only, wherein the following biological and chemical-physical methods may be differentiated.

In chemical-physical phosphorus removal, the dissolved phosphate is precipitated by the addition of precipitating agents. As precipitating agents, $Fe^{3+}$, $Al^{3+}$, $Fe^{2+}$ and $Ca^{2+}$ are predominantly used. Disadvantageously, however, the precipitating agents partly are by-products or waste products of commercial processes and, therefore, contain impurities such as, e.g., heavy metals and organic halogen compounds, which increase the pollutant load of the sewage sludge. Ferrous phosphates, moreover, cannot be taken up by plants. The use of precipitating agents in pure form, on the other hand, is expensive.

For an adequate recovery of phosphorus from solids, such as sewage sludge incineration ash, it is necessary to solubilize chemically bound phosphorus. Solubilizing chemically-physically bound phosphorus to a large extent, however, is only possible using acids and at low pH values. As a rule, solubilization of phosphate is carried out by acidic decomposition using mineral acid, followed by selective precipitation steps. In the Seaborne process, for example, at first an anaerobic sludge treatment is carried out in which the bound phosphorus is subsequently solubilized along with the heavy metals by the addition of acid. The pH is then raised again and the heavy metals are precipitated selectively using $H_2S$ and removed. In a further step, phosphorus is selectively precipitated by adding bivalent metals. These processes, however, are time-consuming and costly.

Enhanced biological phosphorus removal utilizes the capability of polyphosphate-storing or polyphosphate-accumulating microorganisms, in particular bacteria, to accumulate phosphorus as an energy-rich polyphosphate in the form of granula. This process is known as the Bio-P process and is widely used in waste water disposal for the removal of dissolved phosphate. Processes for enhanced biological phosphorus removal are described, e.g., in DD 282 902 A5, DE-A-36 02 736 A1, DE 196 35 391 A1, GB 2 351 284 A, and DE 10 2005 007 408 A1. The phosphorus removed from the waste water stream by biological phosphorus removal is eliminated from the system together with the excess sludge.

Enhanced biological phosphorus removal, however, is not directly applicable for the recovery of chemically bound phosphorus. In phosphorus-containing solids such as sewage sludge incineration ash, however, phosphorus is at least partly present in a chemically bound form. In sewage sludge incineration ash, the phosphorus fully remains as a residue in the ash. Although heavy metals such as Pb, Cd, Cu, Cr, Hg, Ni, and Zn as a rule are present in the ash only as trace elements, the maximum permissible values set in the Rules and Regulations for Fertilizers may nevertheless be exceeded. This necessitates further treatment of the ash. In addition, absent of further treatment, the availability of phosphorus, which in the ash is predominantly present in the form of apatite, is not sufficient in the soil for nutrient supply of plants.

SUMMARY OF THE INVENTION

The prior-art methods for recovering phosphorus require numerous consecutive precipitation steps and accurate metering of the precipitants, which is technically complex on a large scale due to varying quantities of phosphorus in the materials to be treated. Precipitation, moreover, requires introduction of additional chemicals, which is costly and may result in undesired environmental pollution.

The object of the present invention, therefore, was to provide a simple and cost-efficient method for obtaining phosphorus from solids containing heavy metals and phosphates, wherein the phosphorus may be isolated free from heavy metals. It has now been found that phosphorus may efficiently be released from such solids and separated from heavy metals if the solids are subjected to a simultaneous treatment with microorganisms with leaching activity (leaching microorganisms) and phosphate-refixing, in particular polyphosphate-accumulating microorganisms.

The object of the present invention, therefore, is a method of selectively obtaining phosphorus from solids containing heavy metals and phosphates according to claim 1, comprising:

treating the solid containing heavy metals and phosphates using microorganisms comprising leaching microorganisms and polyphosphate-accumulating microorganisms under acidic aerobic conditions for releasing heavy metals and phosphate from the solid and for uptake of the released phosphate by the polyphosphate-accumulating microorganisms; and separating biomass enriched in phosphorus.

It has surprisingly been found that phosphate-refixing microorganisms, in particular polyphosphate-accumulating microorganisms, are capable of bioaccumulation of phosphates even under the acidic conditions under which leaching of heavy metals and phosphates occurs. In this way, it is possible to separate the phosphorus from undesirable heavy metals in the form of biomass so that it is available for further utilization.

Leaching microorganisms as used in accordance with the invention are aerobic sulfur-oxidizing microorganisms, for example sulfur-oxidizing bacteria and archaea as used in known, conventional biological leaching processes ("bioleaching") for obtaining heavy metals from ores. These microorganisms are capable of solubilizing heavy metal sulphides by oxidizing sulphides and elemental sulfur to sulfate resulting in the formation of sulfuric acid. Microorganisms suitable for leaching are—without being limited thereto— microorganisms of the genera *Acidithiobacillus, Leptospirillum, Sulfobacillus, Acidimicrobium, Ferroplasma, Sulfolobus, Acidianus, Metallosphaerea, Fulvimonas, Rhodanobacter, Alicyclobacillus, Dyella, Dokdonella* and *Acidiphilum*. Examples are microorganisms of the species *Acidithiobacillus thiooxidans, Acidithiobacillus ferrooxidans, Acidithiobacillus caldus, Acidithiobacillus albertensis, Leptospirillum ferrooxidans, Leptospirillum ferriphilum, Fulvimonas soli, Rhodanobacter thiooxydans, Alicyclobacillus ferrooxydans, Dyella yeojuensis, Dokdonella koreensis* and *Acidiphilum cryptum*. *Acidithiobacillus* species such as *Acidithiobacillus thiooxidans* and *Acidithiobacillus ferrooxidans* are particularly preferred leaching microorganisms.

Phosphate-refixing, in particular polyphosphate-accumulating microorganisms, for example polyphosphate-accumulating bacteria (also known as Bio-P bacteria), are aerobic microorganisms which take up more phosphorus than usual and store it in the cell. Phosphate-refixing and polyphosphate-accumulating bacteria are found, as is well known, e.g, in sewage treatment plants, for instance in the Bio-P tank and in anaerobically stabilized sewage sludge (digested sludge), which is a mixture of about 95 to 99% of water and 5 to 1% of solids. In case of anaerobic/anoxic conditions in the activated sludge of Bio-P tanks or as in the digestion tower, numerous aerobic microorganisms loose theft capability of nutrient uptake. Under such stress conditions, polyphosphate-accumulating microorganisms utilize the energy from the stored polyphosphates for the uptake of nutrients by releasing phosphate. When oxygen is subsequently available again to the bacteria, the bacteria replenish their energy stores in the form of polyphosphate, with more phosphate being taken up in the process than was previously released. Phosphate-accumulating microorganisms in a state following anaerobic stress conditions which replenish their phosphate reservoir under aerobic conditions are in the following also referred to as "anaerobically conditioned" polyphosphate-accumulating microorganisms. The use of "anaerobically conditioned" microorganism is preferred. Exemplary polyphosphate-accumulating microorganisms which may be used in the method of the invention are—without being limited thereto— microorganisms of the genera *Pseudomonas, Aeromonas, Rhodocyclus, Tetrasphera,* and *Acinetobacter*.

According to the invention, sulfur-oxidizing leaching microorganisms and phosphate-refixing, in particular polyphosphate-accumulating microorganisms, are used jointly as a leaching liquid, wherein the phosphate released under the acidic conditions of the method is accumulated by the phosphate-refixing and polyphosphate-accumulating microorganisms. The microorganisms may originate from single cultures or, for example, from soil samples or sludges. They may be cultured individually or jointly in suitable media, in the case of polyphosphate-accumulating microorganisms may optionally be exposed to anaerobic stress in order to deplete the phosphate reservoirs, and then they may be used as a mixture under acidic conditions in the method of the invention. Typically, the microorganisms used in the method of the invention comprise various kinds of leaching microorganisms and phosphate-refixing, in particular polyphosphate-accumulating microorganisms. Depending on the starting material for the microorganisms, the mixture used in accordance with the invention may thus also contain other aerobic and anaerobic microorganisms.

Preferably, however, the mixture of microorganisms used in the method of the invention is obtained by enriching sulfur-oxidizing leaching microorganisms in an aqueous starting material containing anaerobically conditioned, polyphosphate-accumulating microorganisms. Examples of starting materials containing polyphosphate-accumulating microorganisms are anaerobically stabilized sewage sludge or material as is found in the anaerobic stage of a Bio-P tank. Anaerobically stabilized sewage sludge is preferred as a starting material. Enrichment of sulfur-oxidizing microorganisms is properly achieved by culturing such starting material, which usually also contains sulfur-oxidizing microorganisms as endogenous microorganisms, in particular *Acidithiobacillus thiooxidans* and *Acidithiobacillus ferrooxidans*, under addition of an oxidizable sulfur source, e.g., in the form of elemental sulfur or of sulphides, preferably together with iron (II) sulfate ($FeSO_4$), under aerobic conditions. Sulfur-oxidizing microorganisms utilize $CO_2$ as a carbon source and grow predominantly under these conditions. Optionally, however, it is also possible to add desired sulfur-oxidizing microorganisms to the starting material, which are then enriched. Culturing preferably is effected at a temperature between 15 and 37° C., preferably between 20 and 30° C. Due to the fact that sulfur-oxidizing microorganisms such as *Acidithiobacillus thiooxidans* produce large quantities of sulfuric acid in the process, the pH value of the starting material, which is usually between 7 and 8, may drop to less than 2. It has surprisingly been found that the polyphosphate-accumulating microorganisms tolerate culturing under these acidic conditions. Culturing is continued until the pH has reached the desired value, advantageously a pH value of 4.0 or less, more preferably between 1.0 and 3.5, for example between 1.5 and 3.5 or 2.0 and 3.5, and most preferably between 1.5 and 2.5, for example between 2.2 and 2.5. The solid particles then are preferably removed. The culture liquid obtained upon culturing, which contains the sulfur-oxidizing and polyphosphate-accumulating microorganisms, may be used as a leaching liquid in the method of the invention. Such a leaching liquid may correspondingly also contain other aerobic or anaerobic microorganisms as are present in the starting material.

The thus obtained microbial composition which contains enriched sulfur-oxidizing leaching microorganisms and anaerobically conditioned polyphosphate-accumulating microorganisms is also subject of the invention.

Solids that may be treated in accordance with the method of the invention for obtaining phosphates are leachable solids containing heavy metals and phosphates. Such solids may occur naturally or may be obtained following heat treatment or dehydration. Examples of solids that may advantageously be treated using the method of the invention are combustion ashes such as sewage sludge incineration ash, meat and bone meal, industrial slags, soil material, sludges, landfills, and liquid manure.

In the treatment of the solids in accordance with the invention, the leaching microorganisms oxidize the heavy metal sulphides and thus solubilize the metals. In parallel, chemically bound phosphorus is released and solubilized as well under these acidic leaching conditions. If the sulfur content of the treated solids is very low, treatment may also be carried out by adding oxidizable sulfur in the form, for example, of elemental sulfur or of sulphides.

The method of the invention is usually carried out at a pH value of $\leq 4.0$, more preferably of between 1.0 and 3.5, for example between 1.5 and 3.5 or 2.0 and 3.5, and most preferably of between 1.5 and 2.5, for example between 2.2 and 2.5. A person skilled in the art will be capable of determining the optimum pH value by simple experiments and keeping it stable if necessary.

The method of the invention is usually carried out at a temperature of between 15 and 30° C. and preferably between 20 and 25° C.

Due to the surprising tolerance of the low pH values by the phosphate-refixing and polyphosphate-accumulating bacteria, they are still capable of enhanced accumulation of released phosphate. This may take place very rapidly, for oxygen is sufficiently present for the aerobic-type microorganisms as an electron acceptor. These conditions allow exponential growth of the phosphate-refixing and polyphosphate-accumulating bacteria, and the leached phosphate is refixed or accumulated in the form of polyphosphate as an endogenous energy carrier. The leached heavy metals remain in solution.

As a rule, treatment of the solids containing heavy metals and phosphorus takes place by percolating acidic leaching liquid containing sulfur-oxidizing and anaerobically conditioned polyphosphate-accumulating leaching microorganisms through the medium to be treated. This treatment may, for instance, have the form of a dump or heap leach or of stack percolation (wet stacking). Advantageously the solid to be leached is present in a percolator through which the acidic leaching liquid containing the sulfur-oxidizing leaching microorganisms and the anaerobically conditioned, polyphosphate-accumulating microorganisms is percolated. The leaching liquid is present in a reservoir, suitably in a stirred reactor. The percolated leaching liquid is preferably recycled into the percolator, preferably via the reservoir. Such an operating mode improves the leaching rate. The continuous recycling moreover ensures an optimum dissolution ratio of the heavy metals and the phosphorus, as well as a continuous supply of microorganisms.

The phosphate-enriched biomass thus produced is removed from the leaching solution, for example by centrifuging or filtering. Removed microorganisms may continuously be replaced with fresh microorganisms. Removal of the phosphorus-enriched biomass suitably is carried out when the phosphate concentration in the leaching liquid has reached a minimum. In addition to the biomass, optionally, also the leaching liquid enriched in heavy metals and/or the solid materials depleted in heavy metals may be removed and supplied for reuse.

The accumulated phosphorus is plant available and free from undesirable heavy metals. The resulting biomass may be used as a plant available nutrient source, for example as an organic fertilizer, or for soil improvement. The above-described method thus allows bio-leaching of solids containing metals and rich in phosphorus, and simultaneous selective recovery of phosphorus. Hence, the method of the invention is a cost-efficient and environmentally compatible recycling method for the nutrient phosphorus. At the same time, the method is excellent for decontaminating polluted solids, which are depleted in heavy metals, and thus for soil remediation. The solids depleted in heavy metals may readily be recycled, for instance as construction materials, in particular for road construction, as the threshold for contamination with heavy metals required for such a use is not exceeded. In addition, the method of the invention may concurrently be used for efficient mobilization and recovery of heavy metals from the treated solid materials, for instance by concentrating heavy metals contained in the resulting leaching solution by membrane assemblies.

BRIEF DESCRIPTION OF THE DRAWINGS

The present invention is illustrated in more detail by the following working example with reference to the accompanying Figures, wherein it is understood that the invention is not limited to this working example.

DETAILED DESCRIPTION OF ILLUSTRATIVE EMBODIMENTS

The following is a working example, where anaerobically conditioned sewage sludge (digested sludge, solids content about 6%) which was obtained from a municipal sewage treatment plant was used as a starting material. Due to the residence time in a digestion tower, this digested sludge contains anaerobically conditioned, polyphosphate-accumulating microorganisms with empty phosphate reservoirs. The samples were collected in 2-liter polypropylene bottles and stored at 4° C. until utilization.

Figure 1:
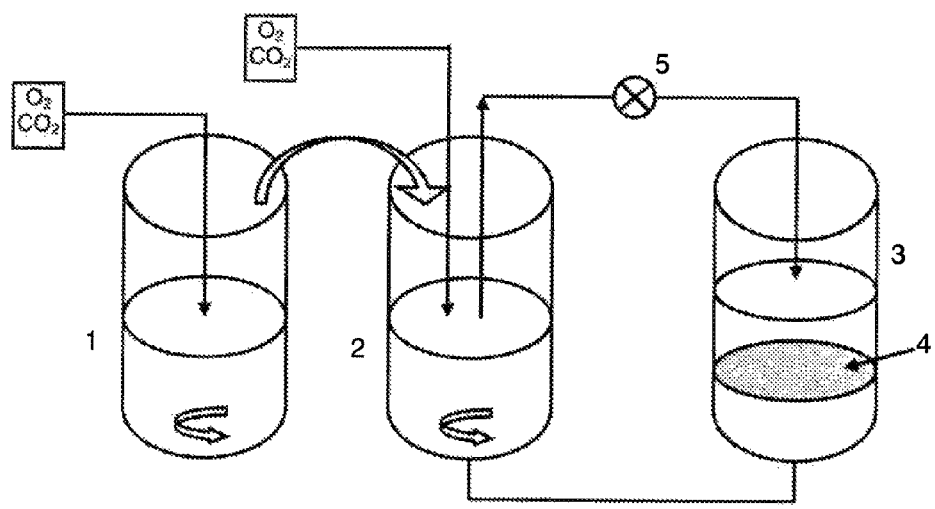
FIG. 1 shows a schematic representation of the method of the invention.
Figure 2:
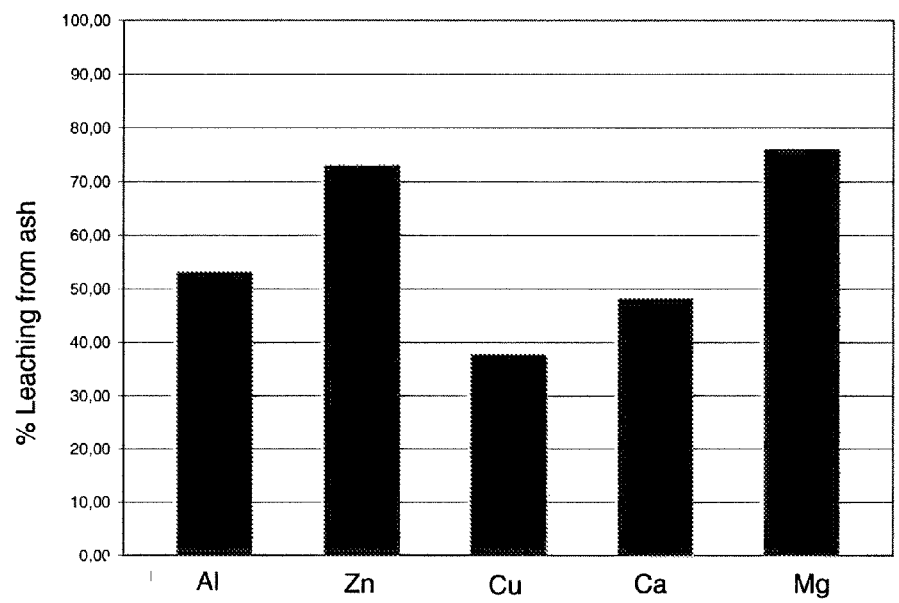
FIG. 2 shows the leaching rate of metals from sewage sludge incineration ash using *Acidithiobacillus* enriched digested sludge (AEDS) following treatment for a period of 11 days. The indications refer to the total metal content in the sewage sludge incineration ash.

Sulfur-oxidizing leaching microorganisms were enriched in the digested sludge adding elemental sulfur as an energy source and supplying $CO_2$ as a carbon source. Referring to FIG. 1, to 2 liters of anaerobically conditioned sewage sludge in a 2-liter stirred reactor (1) 10 g/l of elemental sulfur were added with stirring (250 rpm) and under aeration with oxygen- and carbon dioxide-containing compressed air. Enrichment was performed at room temperature (25° C.) without addition of further nutrients. The pH was measured daily in order to monitor bacterial growth. After a pH value of 2.3 to 2.4 had been reached (after about 22 days), the batch was centrifuged at 25,000 g for 20 min. The supernatant enriched in sulfur-oxidizing leaching microorganisms and still containing polyphosphate-accumulating microorganisms (about 800 ml; in the following referred to as AEDS) was transferred into a second stirred reactor (2) and used as a leaching solution. The residue was discarded.

The stirred reactor (2) is in communication with a percolator (3) including glass fritt (4) on which the solid to be leached is present. In the example described herein, 2 g of sewage sludge incineration ash were used.

Using a peristaltic pump (5) (flow rate 25 ml/min), the AEDS was transferred from stirred reactor (2) into percolator (3) and via glass fritt (4) was recycled together with the solid to be leached into reactor (2), this cycle being maintained for 11 days. The pH remained substantially stable in this operation mode. Sampling (about 7 ml) took place every 24 h, with the samples being filtered by a 0.45-μm filter.

Concentrated $HNO_3$ was added to samples intended for heavy metal analysis (ratio of 1:3). The proportion of heavy metals released by the AEDS was determined after 11 days of treatment by ICP-MS (Inductively Coupled Plasma—Mass Spectrometry). FIG. 2 shows the content of some heavy metals in solution relative to the total content of heavy metals in the sewage sludge incineration ash. Accordingly, between 40% (copper) and 70% (zinc) of the heavy metals contained in the sewage sludge incineration ash were solubilized.

Figure 3:
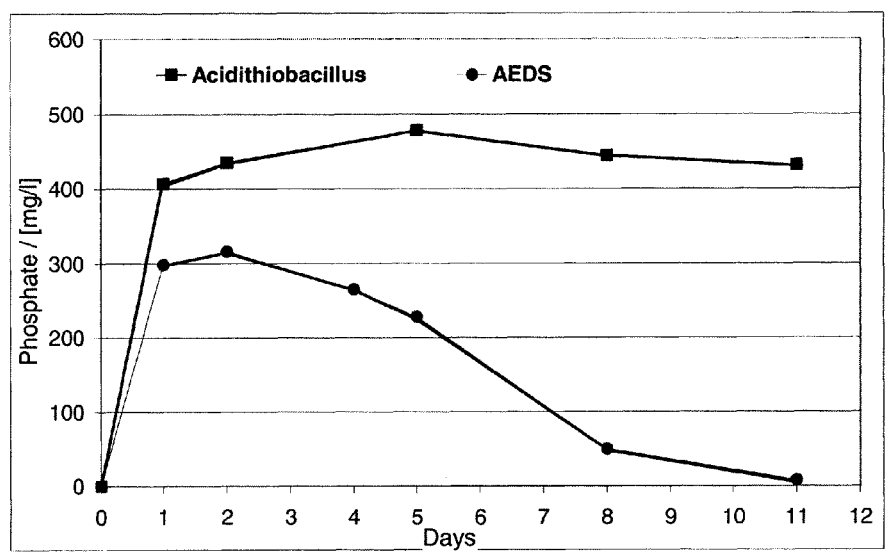
FIG. 3 shows the quantity of dissolved phosphate for AEDS (circles) in comparison with a pure Acidithiobacillus culture (squares) over a period of 11 days.

The phosphorus content of AEDS was determined using ion chromatography and photometric measurements. The dissolved phosphate, or the phosphate accumulation by phosphate-accumulating bacteria contained in AEDS over the course of time, is shown in FIG. 3 (circles). About 2-4 days after treatment of the sewage sludge incineration ash with AEDS, a marked turbidity of the AEDS was observed which was caused by the growth of the phosphate-accumulating bacteria present in the leaching solution. This was furthermore the moment at which bioaccumulation of the phosphorus released by bio-leaching increased markedly. As may be seen in FIG. 3, due to the accumulation the quantity of dissolved phosphate decreased from about 300 mg/l on Day 3 to about 0 mg/ml on Day 1. If, however, a pure culture of *Acidithiobacillus* in a specifically optimized nutrient medium not containing any phosphate-accumulating bacteria was used, phosphorus accumulation from the solution largely was absent (FIG. 3, squares).

When the phosphorus content in the solution had reached a minimum value, the phosphate-rich biomass was separated from the still dissolved heavy metals by centrifugation.

The method of the invention thus enables efficient bio-leaching of metal-containing and phosphorus-rich solids while at the same time allowing a selective recovery of phosphorus. The mobilized heavy metals may also be recovered from the treated solids.

The invention claimed is:

1. A method of selectively obtaining phosphorus from solids containing heavy metals and phosphates, comprising:
    treating the solid containing heavy metals and phosphorus using microorganisms comprising leaching microorganisms and polyphosphate-accumulating microorganisms under acidic aerobic conditions for releasing heavy metals and phosphate from the solid and for uptake of the released phosphate by the polyphosphate-accumulating microorganisms; and
    separating biomass enriched in phosphorus.

2. The method according to claim 1, wherein the polyphosphate-accumulating microorganisms are anaerobically conditioned polyphosphate-accumulating microorganisms.

3. The method according to claim 1, wherein the treated solid is sewage sludge incineration ash, industrial slags, soil material, sludges, landfills, or liquid manure.

4. The method according to claim 1, wherein treatment of the solid is carried out at a pH value between 2.0 and 3.5.

5. The method according to claim 1, wherein treatment of the solid is carried out at a temperature between 15 and 37° C.

6. The method according to claim 1, wherein treatment takes place with the addition of oxidizable sulfur.

7. The method according to claim 1, comprising the steps of:
    (a) enriching sulfur-oxidizing microorganisms by culturing in a aqueous starting material containing anaerobically conditioned polyphosphate-accumulating microorganisms;
    (b) treating the solid containing heavy metals and phosphorus with the acidic leaching liquid obtained in step (a), under aerobic conditions for releasing heavy metals and phosphate from the solid and for uptake of the released phosphate by the polyphosphate-accumulating microorganisms contained in the culture; and
    (c) separating biomass enriched in phosphorus.

8. The method according to claim 7, wherein the starting material is anaerobically conditioned sewage sludge.

9. The method according to claim 1, wherein the solid is present in a percolator through which acidic leaching liquid containing sulfur-oxidizing leaching microorganisms and anaerobically conditioned polyphosphate-accumulating microorganisms percolates.

10. The method according to claim 9, wherein the percolated leaching liquid is continuously recycled into the percolator.

11. The method according to claim 1, wherein the treatment is carried out supplying fresh leaching microorganisms and polyphosphate-accumulating microorganisms.

12. The method according to claim 1, wherein the separation of the biomass enriched in phosphorus takes place when the phosphate concentration in the leaching liquid has reached a minimum.

13. The method according to claim 1, wherein, in addition to the biomass enriched in phosphorus, the leaching liquid enriched in heavy metals and/or the solid material depleted in heavy metals is/are isolated.

14. The method according to claim 4, wherein treatment of the solid is carried out at a pH value between 2.2 and 2.5.

15. The method according to claim 5, wherein treatment of the solid is carried out at a temperature between 20 and 30° C.

* * * * *